(12) United States Patent
Sahin et al.

(10) Patent No.: US 12,139,415 B2
(45) Date of Patent: Nov. 12, 2024

(54) USE OF NANO-SIZED LANTHANIDE BORATE (DYSPROSIUM BORATE AND ERBIUM BORATE) COMPOUNDS FOR WOUND HEALING PURPOSES AND PRODUCTION METHOD THEREOF

(71) Applicant: YEDITEPE UNIVERSITESI, Istanbul (TR)

(72) Inventors: Fikrettin Sahin, Istanbul (TR); Pakize Neslihan Tasli, Istanbul (TR); Oguz Kaan Kirbas, Istanbul (TR); Taha Bartu Hayal, Istanbul (TR); Batuhan Turhan Bozkurt, Istanbul (TR); Berna Bulbul, Balikesir (TR); Seda Beyaz, Balikesir (TR)

(73) Assignee: Yeditepe Üniversitesi, Istanbul (TR)

( * ) Notice: Subject to any disclaimer, the term of this patent is extended or adjusted under 35 U.S.C. 154(b) by 611 days.

(21) Appl. No.: 17/290,292

(22) PCT Filed: Nov. 15, 2018

(86) PCT No.: PCT/TR2018/050689
§ 371 (c)(1),
(2) Date: Apr. 30, 2021

(87) PCT Pub. No.: WO2020/091699
PCT Pub. Date: May 7, 2020

(65) Prior Publication Data
US 2022/0017378 A1    Jan. 20, 2022

(51) Int. Cl.
*C01F 17/30* (2020.01)
*A61P 17/02* (2006.01)

(52) U.S. Cl.
CPC .............. *C01F 17/30* (2020.01); *A61P 17/02* (2018.01); *C01P 2004/64* (2013.01)

(58) Field of Classification Search
None
See application file for complete search history.

(56) References Cited

U.S. PATENT DOCUMENTS

| 6,352,678 B1 * | 3/2002 | Huguenin | ............... C01B 35/12 |
| | | | 423/263 |
| 2005/0022721 A1 | 2/2005 | Kolis | |

(Continued)

FOREIGN PATENT DOCUMENTS

| CN | 1840045 A | 10/2006 |
| CN | 103131413 A * | 6/2013 |

(Continued)

OTHER PUBLICATIONS

Zeng, Y., et al. "A General Approach to Spindle-Assembled Lanthanide Borate Nanocrystals and Their Photoluminescence upon Eu3+/Tb3+ Doping." Inorg. Chem. 2013, 52, 16, 9590-9596 (Year: 2013).*

(Continued)

*Primary Examiner* — Anthony J Zimmer
*Assistant Examiner* — Zachary John Baum

(57) ABSTRACT

Use of nano-sized lanthanide borate (erbium borate and dysprosium borate) compounds for wound treatment due to their significant level of wound healing effect on the cells is disclosed. In the scope of the invention, the synthesis of nanometer-sized erbium borate and dysprosium borate compound by buffered-precipitation method at room conditions and the use of these compounds in biological applications are discussed.

13 Claims, 4 Drawing Sheets

(56) References Cited

U.S. PATENT DOCUMENTS

2009/0041647 A1 2/2009 Prolss et al.
2011/0002971 A1 1/2011 Hassler et al.

FOREIGN PATENT DOCUMENTS

EP 770392 A2 5/1997
EP 775492 A1 5/1997

OTHER PUBLICATIONS

English translation of CN-103131413-A Description (Year: 2013).*
Zeng, Y., et al. A general approach to spindle-assembled lanthanide borate nanocrystals and their photoluminescence upon Eu3+/Tb3+ doping. Inorg. Chem. 2013, 52, 9590-9596. (Year: 2013).*
Weizhong Gu, et al., Systematic investigation of a new nanoscale bioactive glass on wound healing in vivo in comparison with the clinically applied 45S5 Bioglass, Regenerative Medicine, 2018, pp. 1-13, Science Repository.
J. Bradford Rice, et al., Burden of Diabetic Foot Ulcers for Medicare and Private Insurers, Diabetes Care, 2014, pp. 651-658, vol. 37.
David G. Armstrong, et al., Diabetic Foot Ulcers and Their Recurrence, The New England Journal of Medicine, 2017, pp. 2367-2375, 376:24.
Madalina Elena Grigore, et al., Methods of Synthesis, Properties and Biomedical Applications of CuO Nanoparticles, Pharmaceuticals, 2016, pp. 1-14, 9,75.
Florian J. Heiligtag, et al., The fascinating world of nanoparticle research, Materials Today, 2013, pp. 262-271, vol. 16 No. 7/8.
Paul Martin, et al., Cellular and molecular mechanisms of repair in acute and chronic wound healing, British Journal of Dermatology, 2015, pp. 370-378, 173.
Jun Tian, et al., Topical Delivery of Silver Nanoparticles Promotes Wound Healing, Chem. Med. Chem., 2007, pp. 129-136, 2.

* cited by examiner

USE OF NANO-SIZED LANTHANIDE BORATE (DYSPROSIUM BORATE AND ERBIUM BORATE) COMPOUNDS FOR WOUND HEALING PURPOSES AND PRODUCTION METHOD THEREOF

CROSS REFERENCE TO THE RELATED APPLICATIONS

This application is the national phase entry of International Application No. PCT/TR2018/050689, filed on Nov. 15, 2018, which is based upon and claims priority to Turkish Patent Application No. 2018/16274, filed on Oct. 31, 2018, the entire contents of which are incorporated herein by reference.

TECHNICAL FIELD

The present invention relates to the fact that nano-sized lanthanide borate (erbium borate and dysprosium borate) compounds have therapeutic feature due to their significant level of wound healing effect on the cells.

BACKGROUND

In addition to their stable and powerful luminescence, Erbium borate ($ErBO_3$—$Er(BO_2)_3$) and Dysprosium borate ($DyBO_3$—$Dy(BO_2)_3$) have wide bandwidths and by this means great Vacuum UV transmittance. Thus, they have many applications in the optical and electronic fields such as gas discharge panels, discharge indicator panels, neutron detectors and fluorescent lamps.

In general, these compounds are obtained by the conventional solid-state method. In a typical synthesis, the trioxide lanthanide compound ($Er_2O_3$, $Dy_2O_3$) is mixed with a boron compound containing $B_2O_3$ at high temperature (600-1000° C.) and pressure. The temperature, pressure and lanthanide/boron ratio used affect the crystal structure and properties of the synthesized compound. For example, it was possible to synthesize $Dy_4B_4O_{15}$ as a different dysprosium borate compound at 8 GPa, pressure and a temperature of 1000° C., Hydrothermal method has been developed in the recent years to avoid high temperature and pressure. There is a patent application (US 2005/0022721) filed in this field. As it is known, many physical properties of the materials change and acquire a higher quality when moving from microsizes to nanosizes. Therefore, synthesis in nano-size is important. However, the studies on the synthesis of erbium borate and dysprosium borate compounds in nano-size are very limited. In one of these studies, $DyBO_3$ and $ErBO_3$ nanosheets were obtained by the reaction of $Ln_2O_3$ (Ln: Er, Dy) and $H_3BO_3$ compounds in water at 200° C. in a pressure-resistant sealed Teflon container. The reaction time was 24 hours and the nanoparticles obtained had a thickness of 50 nm and an average size of 1-10 micrometers. This study was carried out by another team by using solid state method without using water. However, as a result of the synthesis, a wide distribution was observed in the particles in micron size. In another study, a general method of lanthanide borate synthesis was provided. In the said method, the lanthanide chloride salts first reacted with NaOH and then reacted with the compound $H_3BO_3$ accompanied by a surfactant (PVP, SDS etc.) in a pressure-resistant Teflon container at 200° C. The size range of the nanoparticles obtained in various forms is very wide: 80-500 nm.

The biology of wound closure is a multi-layered and complex system that has been under research for many years. Today, studies are underway at full steam to develop new treatment methods which are fast, prevent scars and minimize visual disturbance of the patient in the treatment of wounds. Increased incidence of disorders such as diabetes and high blood pressure, which cause refractory chronic wounds, has made it a necessity to develop new wound treatment methods.

It is of great importance to develop modern treatment methods that benefit from new inventions especially in the treatment of chronic wounds, Chronic wounds are the wounds that cannot be adequately healed within a month in the normal treatment process and cause serious decreases in the life quality of the patients. Such wounds, which may prolong from 12 to 16 months and have a probability of relapse of 60 to 70% [1], have an impact on mental health as well as the physical health of the patients. These long-term diseases have also become a serious financial burden on health systems around the world. Only diabetic ulcer treatments in the United Kingdom in 2015 was 5.3 billion pounds [2], and ranged from $9 to $13 billion in the United States in 2012 [3]. The aging population, especially in the developed countries, will bring about an increase in the coming years in the said diseases and the accompanying financial difficulties.

The wound closure can be discussed in four separate phases. The first phase is the phase of homeostasis, i.e. stopping the bleeding. When the wound occurs, the vessels in the wound area narrow and slow down the blood flow to the concerned area. Then the platelet cells come together to cover the gaps in the blood vessels. Finally, coagulation, which is combination of the platelet cells with fibrin filaments, takes place. The homeostasis starts when the wound is opened and occurs very rapidly, Following homeostasis, the inflammatory phase begins wherein the immune system cells are brought to the wound site. These cells remove the cells damaged as a result of the wound, the bacteria and the other pathogens from the site. As a result of inflammation, reddening, pain and warmth occurs at the wound site. After the first two phases, permanent repair of the wound site begins. During the proliferative phase, the tissue at the wound area is regenerated with proteins secreted by the new cells and vascularization takes place to provide nutrients to the new tissue. Finally, in the wound's maturation, or reconstruction phase, programmed death of the cells, which have arrived at the site for wound repair, but are no longer required, takes place, and the proteins that make up the new tissue are rearranged to soften the tissue and make it more durable [4].

The conventional wound treatment method is the closure of the wound with a, dressing made of different materials and containing different agents. One of the major developments in this area is the recognition in the 1960s that keeping the wound surface moist has an important role in the wound healing process. For effective wound treatment, the wound bed should be kept moist while allowing oxygen flow and kept away from physical factors and microorganisms. Although many different methods and agents are used to provide protection against microorganisms and accelerate wound healing, none of these methods show the same success in each wound. Different treatment methods are required to provide the best healing conditions for each of the acute-chronic wounds in different parts of the body resulting from different causes. Different nanoparticles have been shown to be effective in wound treatment. Nanoparticles with known antimicrobial effects, such as silver nanoparticles, both accelerate the treatment of the wound and reduce the risk of infection by protecting the wound from microorganisms (US 2005/0022721).

In the literature, it was determined that the active ingredients of the drugs used for increasing the rate of division of the cells and repairing and healing the wound were not significantly anti-inflammatory or increasing the rate of cell division. In the studies in the literature, the failure in preventing the formation of newly formed scar tissue as well as increasing the rate of division of the cells in the wound site disrupts the reconstruction phase of the scar tissue. The health effects and biological applications of the Erbium borate ($ErBO_3$—$Er(BO_2)_3$) and Dysprosium borate ($DyBO_3$—$Dy(BO_2)_3$) compounds have never been investigated so far.

The European patent application document no. EP775492, an application in the state of the art, discloses use of lanthanide, tin, zinc, manganese, yttrium, cobalt, strontium salts for (i) the treatment of pain associated with at least one cutaneous disorder; (ii) hypertrophic wound closure (cicatrization) control; and/or (iii) the treatment of acne rosacea. The lanthanide salts used in the invention also include dysprosium and erbium salts, and the ions in these salts also include borate. Even two different nanoparticles of the same element can show different characteristics according to the production method and can show different applications [5] [6].

The European patent application document no. EP770392, an application in the state of the art, discloses use of manganese, yttrium or certain lanthanide salts in a cosmetic, dermatological or pharmaceutical composition particularly for the treatment of sensitive skin. The lanthanide salts used in the invention also include dysprosium and erbium salts, and the ions in these salts also include borate.

United States patent application no, US2009041647 (WO2006134141 A2), an application in the state of the art, discloses a method for producing nanoparticulate lanthanide/boron compounds or solid substance mixtures containing the same. This production method comprises the steps of a) mixing i) one or more lanthanide compounds selected from the group consisting of lanthanide hydroxides, lanthanide hydrides, lanthanide chalcogenides, lanthanide halides, lanthanide borates and mixtures thereof, ii) crystalline boron, amorphous boron, boron carbides, boron hydrides and boron halides, and iii) if appropriate, one or more reducing agents; b) reacting the mixture of the components i), ii) and, if appropriate, iii) in the inert solvent by means of applying thermal treatment within a reaction zone; c) subjecting the reaction product obtained by means of thermal treatment to rapid cooling; and d) after cooling, obtaining isometric nanoparticulate lanthanide-boron compounds. The particle size of the nanoparticulated lanthanide-boron compounds is in the range of 2-150 nm.

SUMMARY

The objective of the present invention is to use nano-sized (below 50 nm) erbium borate and dysprosium borate compounds in in vivo biological applications preferably for wound healing.

DETAILED DESCRIPTION OF THE EMBODIMENTS

"Use Of Nano-Sized Lanthanide Borate (Dysprosium Borate and Erbium Borate) Compounds For Wound Healing Purposes and Production Method Thereof" developed to fulfill the objective of the present invention is illustrated in the accompanying figures, in which.

Figure 1:
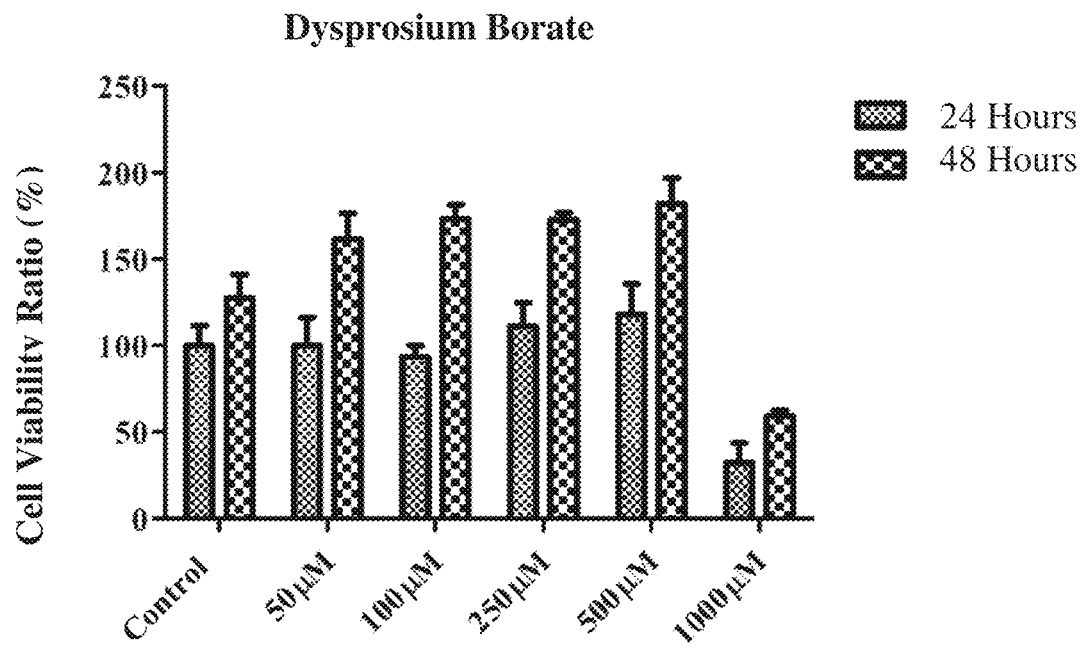
FIG. 1 is a graphical representation of the effect of Dysprosium borate on the viability of the Hacat cell at different concentrations at 24 and 48 hours.
Figure 2:
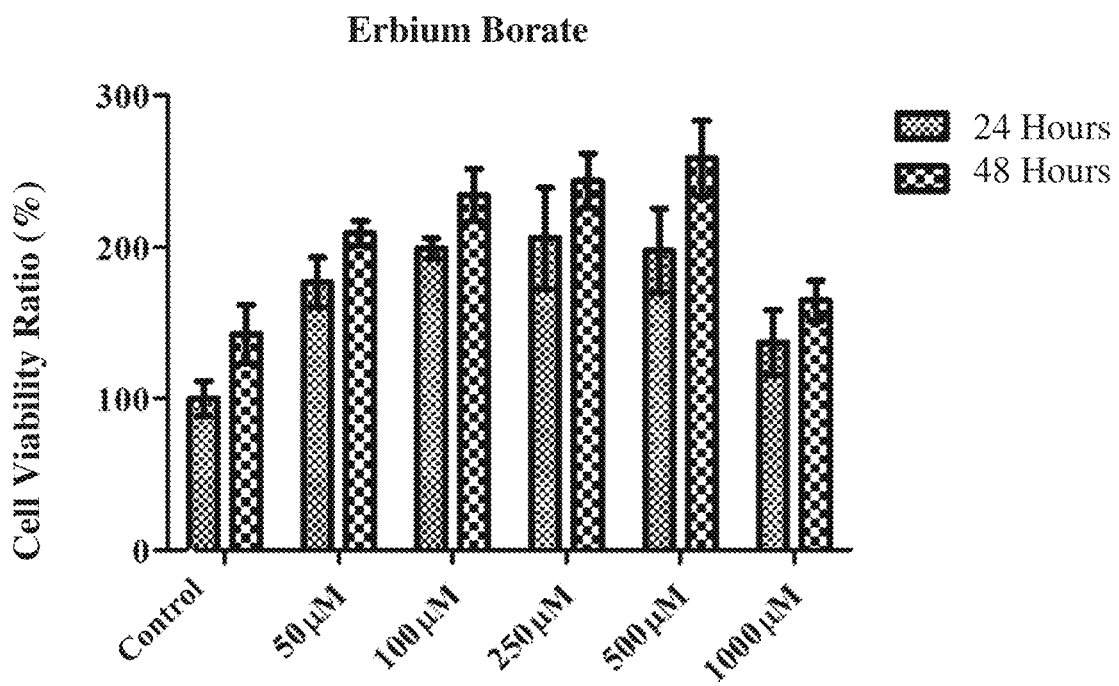
FIG. 2 is a graphical representation of the effect of Erbium borate on the viability of the Hacat cell at different concentrations at 24 and 48 hours.
Figure 3:
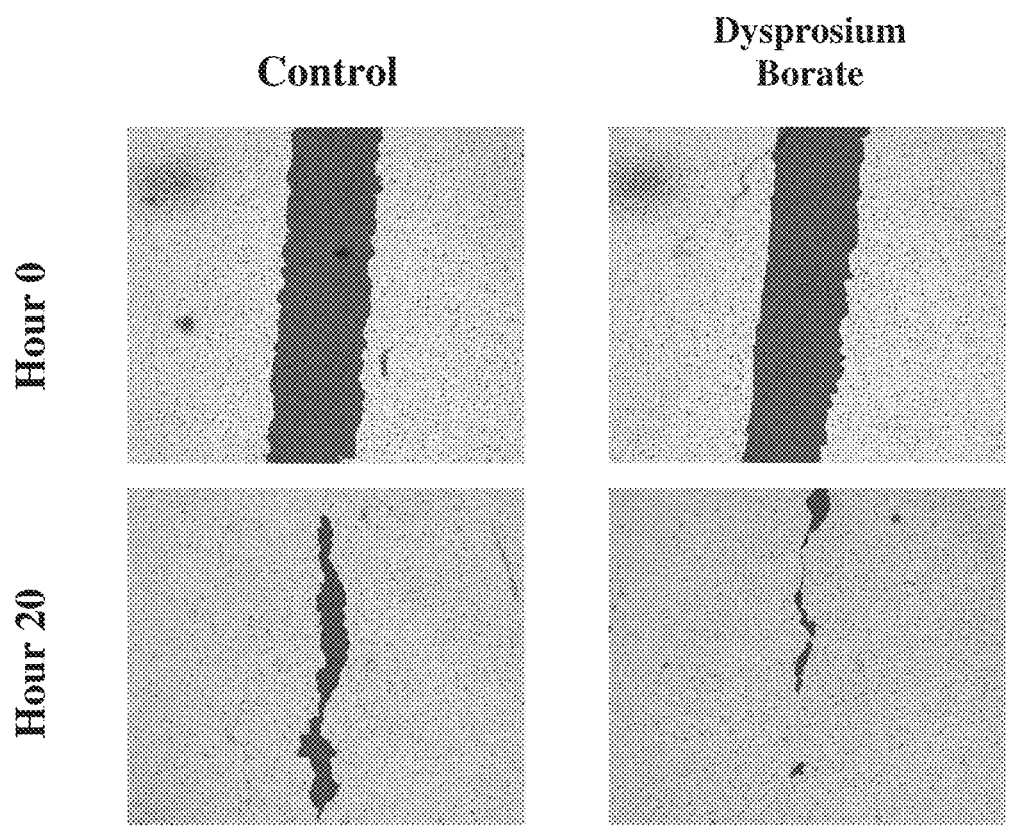
FIG. 3 shows the light microscopy images of the effect of Dysprosium Borate on wound closure. (The dark colors show the areas not containing cells. The image of the cells covering the empty area shows the wound closure potential of the cells.)
Figure 4:
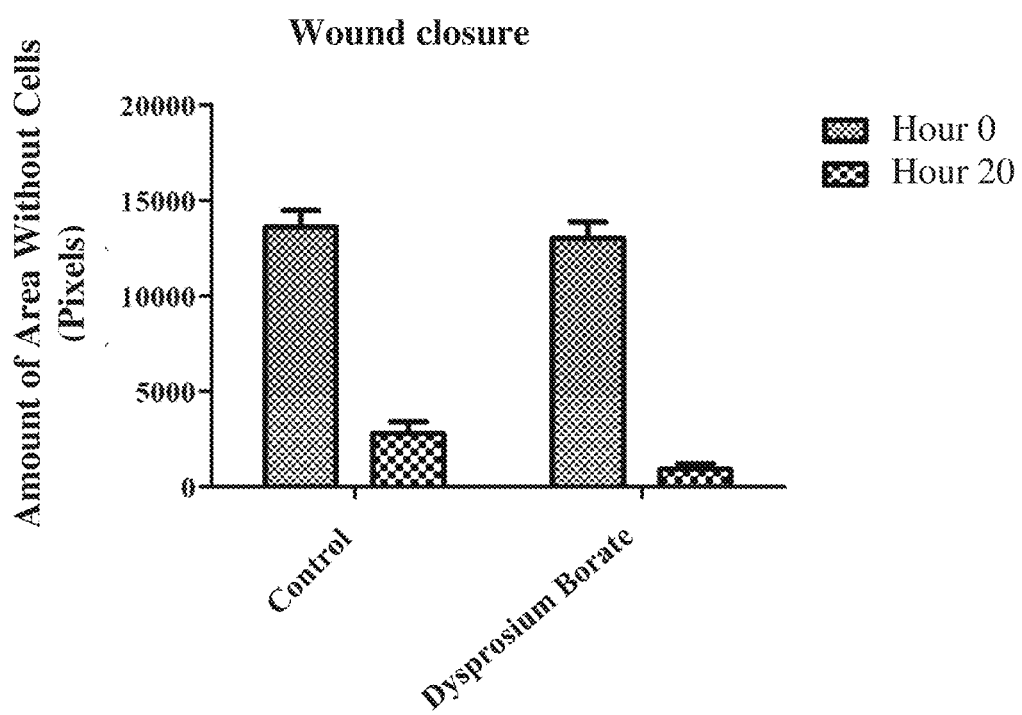
FIG. 4 shows the graphical representation of the effect of Dysprosium Borate on wound closure.
Figure 5:
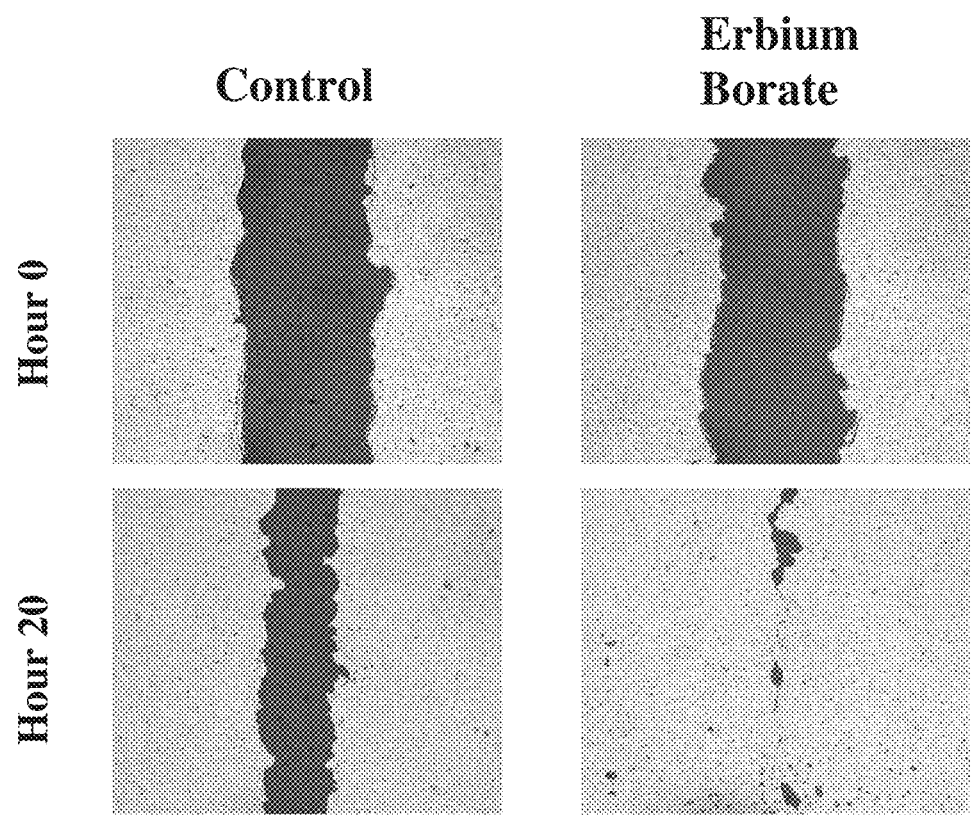
FIG. 5 shows the light microscopy images of the effect of Erbium Borate on wound closure. (The dark colors show the areas not containing cells. The image of the cells covering the empty area shows the wound closure potential of the cells.)
Figure 6:
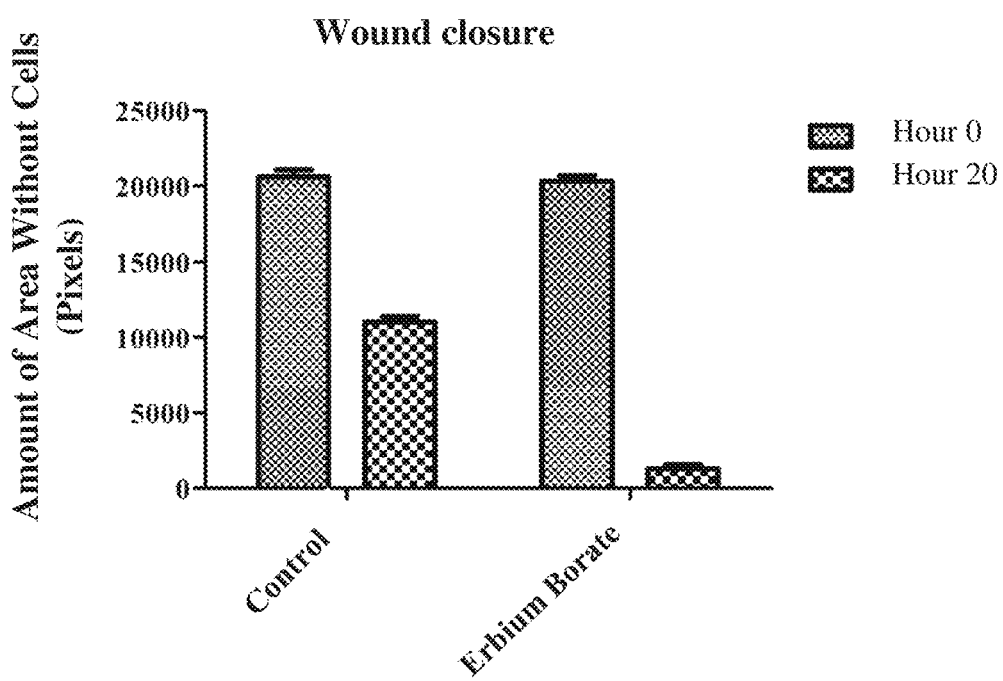
FIG. 6 shows the graphical representation of the effect of Dysprosium. Borate on wound closure.
Figure 7:
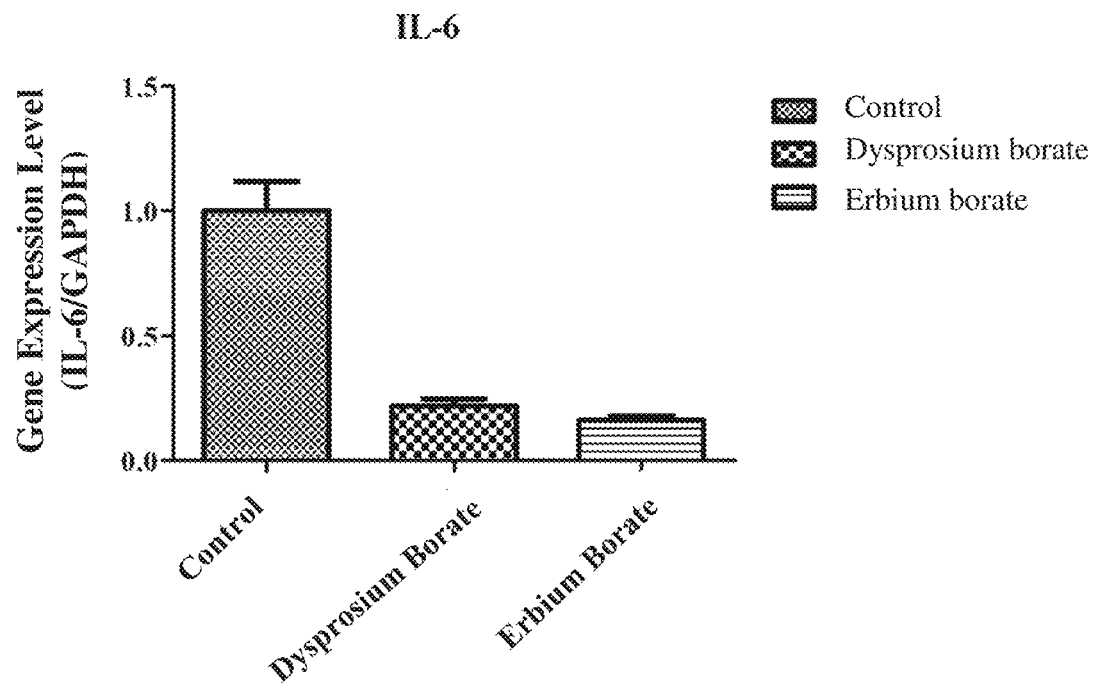
FIG. 7 shows the graphical representation of the effects of Dysprosium and Erbium Borate application on the expression level of IL-6 gene.
Figure 8:
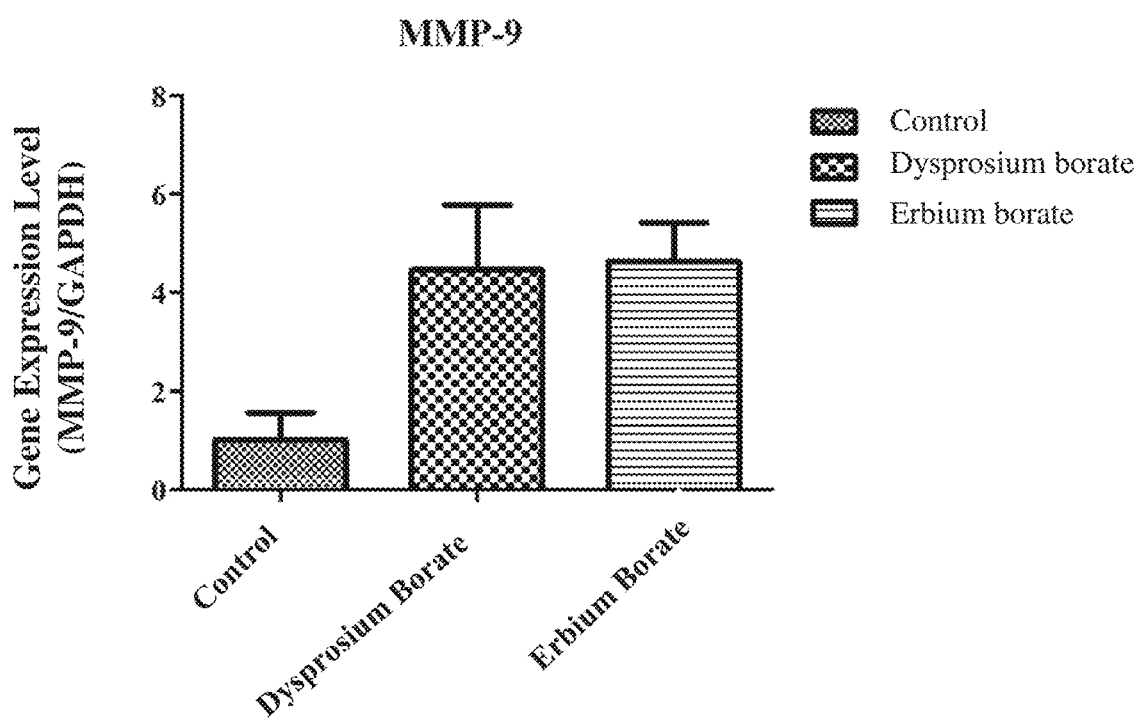
FIG. 8 shows the graphical representation of the effects of Dysprosium and Erbium Borate application on the expression level of MMP-9 gene.

The present invention relates to the fact that nano-sized lanthanide borate (erbium borate and dysprosium borate) compounds have therapeutic feature due to their significant level of wound healing effect on the cells. The fact that particle sizes of erbium borate and dysprosium borate compounds are below 50 nm allows these compounds to be used in in vivo biological applications. The synthesized nano-sized erbium borate and dysprosium borate compounds have an amorphous structure.

In the scope of the invention, the synthesis of nanometer-sized lanthanide borate (erbium borate and dysprosium borate) compound by buffered-precipitation method at room conditions and the use of these compounds in biological applications are discussed. The process steps of this method are as follows:

5—Sodium hydroxide and boric acid substances were mixed with each other in a certain stoichiometric ratio (stoichiometric ratio of 1:2), dissolved in distilled water and a borate buffer with a pH value of 8 to 9.5 was prepared.

6—Lanthanide nitrate (Erbium nitrate or Dysprosium nitrate) and PEG (400 to 20000 Da) were dissolved again in a certain amount of distilled water in a separate beaker in an appropriate stoichiometric ratio.

7—Lanthanide nitrate (Erbium nitrate or Dysprosium nitrate) —PEG solution and Borate buffer solution were stirred for 30 minutes at 2000 rpm under a mechanical stirrer.

8—The obtained products were washed with distilled water 4 times and then dried in an oven at 60° C. for 24 hours to remove the impurities.

The nano-sized erbium borate and dysprosium borate compounds are synthesized using the buffered-precipitation synthesis method and this synthesis method utilizes the ability of $NaOH/H_3BO_3$ buffer solution to keep the pH of the reaction medium constant between 8 and 9.5. The synthesis method used is a method which is much easier, economical and suitable for fabrication in comparison to the hydrothermal and solid-state synthesis methods due to the fact that it can be carried out without any need for high temperature, long reaction times, high pressure and any kind of irradiation. PEG (Polyethylene glycol) added to the medium is a biocompatible surfactant. It allows the obtained particles to be obtained in smaller sizes (50 nm and below) and to be easily dispersed in water. In order to be able to use erbium borate and dysprosium borate compounds in biological applications and to obtain smaller nanoparticles, PEGs and other biocompatible surfactants with different molecular weights can be used during or after the reaction.

PEG is a biocompatible surfactant. In the method described above, it is also possible to carry out the reaction without the use of surfactants such as PEG. In this case, only 10 mmol of lanthanide nitrate is dissolved in 20 ml of water in a beaker. The purpose of using PEG at the reaction is to obtain lead borate nanoparticles having smaller particle sizes. On the other hand, in the case that PEG is used, lanthanide nitrate and PEG (400 to 20000 Da) are dissolved in 200 ml of distilled water in a stoichiometric ratio of 1:1.5.

EXPERIMENTAL STUDIES

4. Culturing of the Cells

Human skin keratinocyte cells (HACAT) were cultured in Dulbecco's modified Eagle's medium (DMEM) containing 10% fetal bovine serum (Invitrogen) and 1% PSA (Biological Industries, Beit Haemek, Israel) at a temperature of 37° C. in cell culture incubators with 5% $Ca_2$ medium.

5. Toxicity

After the cells were seeded in 96-well culture plates (Corning Glasswork, Corning, NY) at 5000 cells/well in Dulbecco's modified Eagle's medium (DMEM) containing 10% fetal bovine serum (Invitrogen) and 1% PSA (Biological Industries, Beit Haemek, Israel), the viability levels of the cells were measured on day 1 and 2. Cell viability was measured by using 3-(4,5-di-methyl-thiazol-2-yl)-5-(3-carboxy-methoxy-phenyl)-2-(4-sulfo-phenyl)-2H-tetrazolium (MTS)-method (CellTiter96 AqueousOne Solution; Promega, Southampton, UK). 10 µl MTS solution was added onto the cells within a 100 µl medium and they were incubated at 37° C. in dark for 2 hours. After the incubation process, cell viability was observed by performing absorbance measurement via ELISA plate reader (Biotek, Winooski, VT) device at 490 nm wavelength.

6. Wound Healing

The wound scratch method was used to determine the migration potential of human skin keratinocyte cells (HACAT). In this method, 24 hours after the cells were seeded in 24-well plates in three replicates at 10,000 cells per well, the cell monolayer was cut (slit) in a straight direction with the aid of a 200 µl pipette tip and the wound scratch closure was observed. After the slit was formed, the medium on the cells was discharged and non-toxic doses of Dyspmosium and Erbium Borate according to the results obtained from the toxicology tests were added to the cells except the ones in the control group. The wound scratch closure was measured at hours 0 and 20 by using Carl Zeiss AxioVision Rel. 4.8 software program and the wound closure process was evaluated by comparing the Dysprosium and Erbium Borate administration groups and the control group.

REFERENCES

[1]. Tian, Jun, et al. "Topical delivery of silver nanoparticles promotes wound healing." *ChemMedChem* 2.1 (2007): 129-136.

[2]. Rice, J. Bradford, et al. "Burden of diabetic foot ulcers for medicare and private insurers." *Diabetes care* 37.3 (2014): 651-658.

[3]. Armstrong, David G., Andrew J M Boulton, and Sicco A. Bus. "Diabetic foot ulcers and their recurrence." *New England Journal of Medicine* 376.24 (2017): 2367-2375.

[4]. Martin, Paul, and R. Nunan "Cellular and molecular mechanisms of repair in acute and chronic wound healing." *British Journal of Dermatology* 173.2 (2015): 370-378.

[5]. Grigore, Madalina Elena, et al. "Methods of synthesis, properties and biomedical applications of CuO nanoparticles." *Pharmaceuticals* 9.4 (2016). 75

[6]. Heiligtag, Florian J., and Markus Niederberger "The fascinating world of nanoparticle research." *Materials Today* 16.7-8 (2013): 262-271.

What is claimed is:

1. A method for producing nano-sized lanthanide borate compounds, comprising the steps of
    preparing a borate buffer solution by dissolving and mixing sodium hydroxide and boric acid in distilled water,
    dissolving lanthanide nitrate in distilled water in a separate beaker to obtain a lanthanide nitrate solution,
    mixing the lanthanide nitrate solution with the borate buffer solution to obtain a product,
    washing and drying the product to remove impurities.

2. The method according to claim 1, wherein the sodium hydroxide and the boric acid are mixed in a stoichiometric ratio of 1:2.

3. The method according to claim 1, wherein the borate buffer solution maintains a pH value of a reaction medium between 9 and 9.5.

4. The method according to claim 1, wherein, in the step of mixing the lanthanide nitrate solution and the borate buffer solution, the lanthanide nitrate solution and the borate buffer solution are stirred for 30 minutes at 2000 rpm under a mechanical stirrer.

5. The method according to claim 1, wherein the product is washed with the distilled water 4 times and then dried in an oven at 60° C. for 24 hours to remove the impurities.

6. The method according to claim 1, wherein 10 mmol of the lanthanide nitrate is dissolved in 20 ml of the distilled water.

7. The method according to claim 1, wherein, in a case that the lanthanide nitrate is dissolved in the distilled water, PEG (Polyethylene Glycol) is also dissolved in the distilled water together with the lanthanide nitrate.

8. The method according to claim 1, wherein particle sizes of the nano-sized lanthanide borate compounds are below 50 nm.

9. The method according to claim 1, wherein the nano-sized lanthanide borate compounds are Erbium borate.

10. The method according to claim 1, wherein the nano-sized lanthanide borate compounds are Dysprosium borate.

11. The method according to claim 2, wherein, in a case that the lanthanide nitrate is dissolved in the distilled water, PEG is also dissolved in the distilled water together with the lanthanide nitrate.

12. The method according to claim 3, wherein, in a case that the lanthanide nitrate is dissolved in the distilled water, PEG is also dissolved in the distilled water together with the lanthanide nitrate.

13. The method according to claim 4, wherein, in a case that the lanthanide nitrate is dissolved in the distilled water, PEG is also dissolved in the distilled water together with the lanthanide nitrate.

\* \* \* \* \*